US00PP18885P2

(12) United States Plant Patent
Egger

(10) Patent No.: US PP18,885 P2
(45) Date of Patent: Jun. 3, 2008

(54) ***CAMPANULA* PLANT NAMED 'PINK OCTOPUS'**

(50) Latin Name: ***Campanula* hybrid**
Varietal Denomination: Pink Octopus

(75) Inventor: Janet N. Egger, Wilsonville, OR (US)

(73) Assignee: Terra Nova Nurseries, Inc., Canby, OR (US)

( * ) Notice: Subject to any disclaimer, the term of this patent is extended or adjusted under 35 U.S.C. 154(b) by 43 days.

(21) Appl. No.: 11/639,124

(22) Filed: Dec. 13, 2006

(51) Int. Cl.
*A01H 5/00* (2006.01)

(52) U.S. Cl. ..... Plt./263

(58) Field of Classification Search ..... Plt./263
See application file for complete search history.

*Primary Examiner*—Annette H Para
(74) *Attorney, Agent, or Firm*—Klarquist Sparkman, LLP

(57) ABSTRACT

A new and distinct *Campanula* plant substantially as shown and described, characterized by deep green incised leaves, and large purple pink flowers, with lobes cut into linear segments, octopus-like.

1 Drawing Sheet

Botanical Classification: *Campanula* hybrid.
Variety Denomination: 'Pink Octopus'.

The present invention relates to a new and distinct cultivar of *Campanula* plant and given the cultivar name of 'Pink Octopus'. *Campanula* is in the family *Campanulaceae*. *Campanula* 'Pink Octopus' is a F2 seedling of a cross between *Campanula takesimana* 'Beautiful Trust' (U.S. Plant Pat. No. PP12,815), as the seed parent, and *Campanula punctata* 'Pink Chimes' (U.S. Plant Pat. No. PP13,156), as the pollen parent.

This new and unique *Campanula* is distinguished by:

1. Large, purple pink flowers, with lobes cut into linear segments, octopus-like.
2. Deep green, glossy leaves with incised margins.
3. Very low seed set resulting in longer bloom time.

This new cultivar has been reproduced only by asexual propagation (tissue culture). Each of the progeny exhibits identical characteristics of the original plant. Asexual propagation by division and tissue culture using standard micropropagation techniques with terminal and lateral shoots, as done in Canby, Oreg., shows that the foregoing characteristics and distinctions come true to form and are established and transmitted through succeeding propagations. The present invention has not been evaluated under all possible environmental conditions. The phenotype may vary with variations in environment without a change in the genotype of the plant.

BRIEF DESCRIPTION OF THE DRAWING

The photograph shows *Campanula* 'Pink Octopus' growing in a two gallon container in a sunny greenhouse in August in Canby, Oreg.

DETAILED PLANT DESCRIPTION

The following is a detailed description of the new *Campanula* based on observations of two year old specimen grown in a two gallon container outside in full sun under typical weathers in Canby, Oreg. Canby is Zone 8 on the USDA Hardiness map. Temperatures range from a high of 95 degrees F. in August to 32 degrees F. in January. Normal rainfall in Canby is 42.8 inches per year. The color descriptions are all based on The Royal Horticultural Society Colour Chart.

Plant:

*Form.*—Rosette-forming herbaceous perennial.
*Hardiness.*—USDA Zone 5–8.
*Size.*—Foliage is 29 cm tall from the ground to the top of the foliage and 40 cm wide.
*Habit.*—Upright, clumping, rhizomatous.
*Vigor.*—Excellent.
*Roots.*—Main root Grey Brown 199A, side roots Yellow White 158A to 158C; plants grow easily from divisions.

Leaf:

*Type.*—Simple.
*Arrangement.*—Basal.
*Shape.*—Ovate to broadly ovate.
*Venation.*—Main central vein with secondary veins palmate.
*Margins.*—Incised and doubly serrate.
*Apex.*—Acuminate.
*Base.*—Attenuate.
*Blade size.*—8 to 9 cm long and 5to 9cm wide.
*Surface center.*—Glossy, glabrous, thick and leathery.
*Petiole size.*—17 to 20 cm long and 3 mm wide.
*Petiole surface texture.*—Glabrous.
*Petiole color.*—Yellow Green 148B with Greyed Purple 183A in sun.
*Leaf color.*—Topside — Closest to Green 139A. Bottom side — Closest to Yellow Green 147B.

Inflorescence:

*Type.*—Panicle with 20 to 50 flowers.
*Peduncle.*—40 cm tall, glabrous, Yellow Green 148A changing in sun to Greyed Orange 165A, leaves ovate, 6 cm long and 3 cm wide, with petioles decreasing in size from 11.5 cm to sessile, internodes 2.5 to 6 cm.
*Pedicel.*—1 to 15 mm long and 1 mm wide, pubescent, Yellow Green 148A.
*Bloom period.*—June through August in Canby, Oreg.

Flower bud:

*Size.*—1.2 cm wide and 3.5 cm deep.

*Shape.*—Ovoid, whisk-like.

*Surface texture.*—Pubescent on petal margins.

*Color.*—Red Purple 71A to 70A, but slightly duller.

Flower:

*Type.*—Actinomorphic.

*Shape.*—Campanulate.

*Size.*—4.8 cm deep and 5 cm wide.

*Corolla.*—With 5 lobes, parted almost to the base, narrowly oblanceolate, reflexed, insides are pubescent and back sides are glabrous, each lobe 5 cm long and 6 mm wide, tip acute.

*Color.*—Back side is Purple 77D with vein and edges Red Purple 71A. Inside is White 155D with spots and edges of Red Purple 71A.

*Calyx.*—3.7 cm wide and 12 mm deep, campanulate with lobes flaring, lobes are 16 mm long, 3 mm wide, tips acuminate, backsides pubescent, inside glabrous.

*Calyx color.*—Yellow Green 147B.

*Stamen.*—5, Yellow White 158C before dehiscence, 7 mm long and 1.5 mm wide.

*Pollen color.*—White 155D.

*Pistil.*—White 155D overall, style and stigma 2.2 cm long.

*Fragrance.*—Very slight.

*Lastingness.*—Each flower lasts for about 5 days on the plant.

Fruit:

*Type.*—3-celled capsule.

*Size.*—9 mm deep and 5 mm wide.

*Color.*—Brown 200D.

*Fertility.*—Very low.

Diseases and pests: No diseases found of this new variety or on its parent plant. No known disease resistance. All *Campanula* are susceptible to snails, slugs, and aphids.

COMPARISON TO SIMILAR *CAMPANULA*

Compared to *Campanula* 'Beautiful Trust' (U.S. Plant Pat. No. PP12,815), *Campanula* 'Pink Octopus' has purple pink rather than white flowers.

I claim:

1. A new and distinct *Campanula* plant as herein illustrated and described.

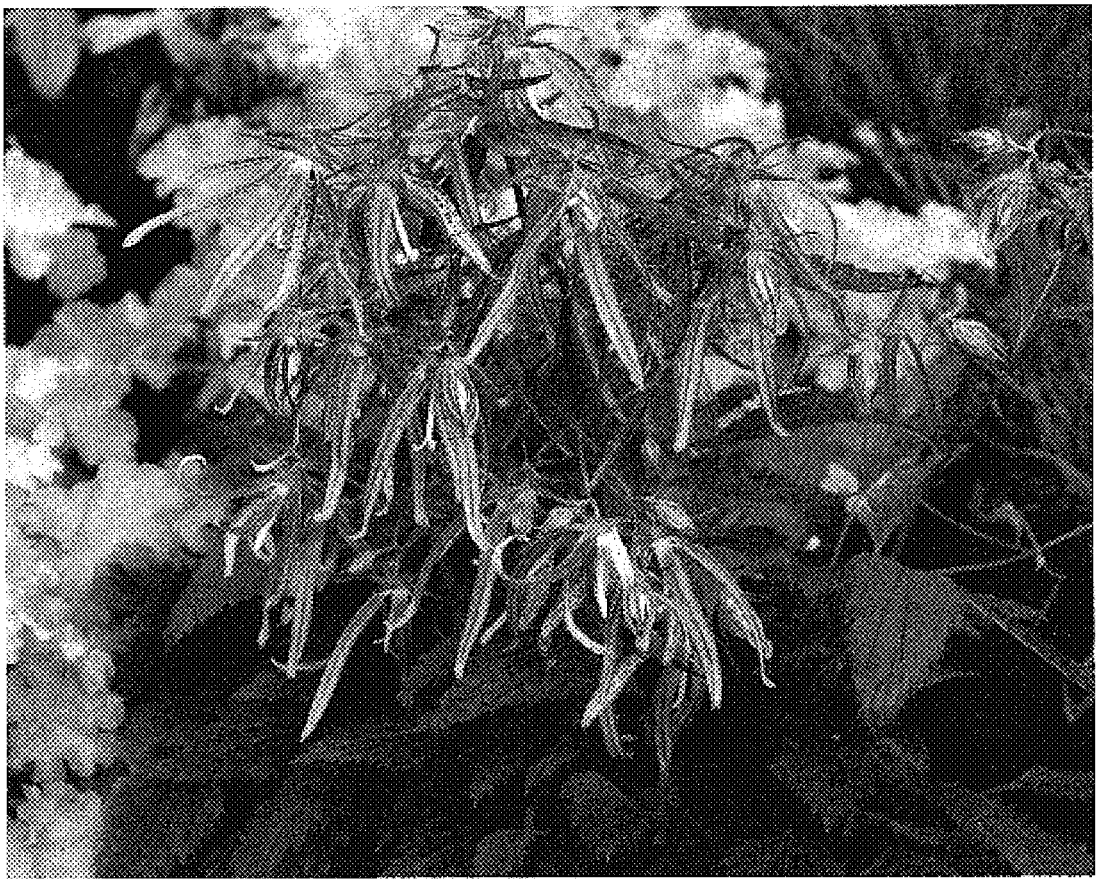

* * * * *